United States Patent
Finkman et al.

(10) Patent No.: US 9,257,763 B2
(45) Date of Patent: Feb. 9, 2016

(54) HYBRID INTERCONNECT

(71) Applicant: GYRUS ACMI, INC., Southborough, MA (US)

(72) Inventors: Shai Finkman, Haifa (IL); Adi Navve, Kfar Saba (IL)

(73) Assignee: GYRUS ACMI, INC., Southborough, MA (US)

( * ) Notice: Subject to any disclaimer, the term of this patent is extended or adjusted under 35 U.S.C. 154(b) by 182 days.

(21) Appl. No.: 13/933,145

(22) Filed: Jul. 2, 2013

(65) Prior Publication Data

US 2015/0011832 A1 Jan. 8, 2015

(51) Int. Cl.
| H05K 7/10 | (2006.01) |
| H05K 7/12 | (2006.01) |
| H01R 12/71 | (2011.01) |
| H01L 23/00 | (2006.01) |
| H01L 27/146 | (2006.01) |
| A61B 1/00 | (2006.01) |
| H05K 1/11 | (2006.01) |
| H05K 3/36 | (2006.01) |

(52) U.S. Cl.
CPC .......... *H01R 12/712* (2013.01); *A61B 1/00131* (2013.01); *H01L 24/81* (2013.01); *H01L 27/1469* (2013.01); *H05K 1/117* (2013.01); *H05K 3/368* (2013.01); *H05K 2201/094* (2013.01); *H05K 2201/09409* (2013.01); *H05K 2201/09709* (2013.01); *H05K 2201/10151* (2013.01); *H05K 2203/041* (2013.01); *H05K 2203/049* (2013.01)

(58) Field of Classification Search
USPC ............................................ 361/767; 439/83
See application file for complete search history.

(56) References Cited

U.S. PATENT DOCUMENTS

| 3,321,656 A | 5/1967 | Sheldon |
| 3,971,065 A | 7/1976 | Bayer |
| 4,253,447 A | 3/1981 | Moore et al. |
| 4,261,344 A | 4/1981 | Moore et al. |
| 4,278,077 A | 7/1981 | Mizumoto |
| 4,429,328 A | 1/1984 | Jones, Jr. et al. |
| 4,467,361 A | 8/1984 | Ohno et al. |

(Continued)

FOREIGN PATENT DOCUMENTS

| EP | 1661506 A1 | 5/2006 |
| GB | 1215383 A | 12/1970 |

(Continued)

OTHER PUBLICATIONS

International Application PCT/US2014/042826 Search Report dated Sep. 8, 2014.

(Continued)

*Primary Examiner* — Andargie M Aychillhum
(74) *Attorney, Agent, or Firm* — D.Kligler IP Services Ltd.

(57) ABSTRACT

A connector for connection to terminals of an integrated circuit. The connector consists of a dielectric substrate having a first side and a second side. The connector has wire bond terminals which are attached to the first side of the substrate and configured to receive wire bonds connected to a first set of the terminals of the integrated circuit. The connector also has solder bump terminals, attached to the second side of the substrate so as to be insulated from the wire bond terminals, the solder bump terminals being configured to be coupled via solder balls with a second set of the terminals of the integrated circuit.

9 Claims, 6 Drawing Sheets

(56) References Cited

U.S. PATENT DOCUMENTS

| | | |
|---|---|---|
| 4,491,865 A | 1/1985 | Danna et al. |
| 4,555,768 A | 11/1985 | Lewis, Jr. et al. |
| 4,569,335 A | 2/1986 | Tsuno |
| 4,573,450 A | 3/1986 | Arakawa |
| 4,576,146 A | 3/1986 | Kawazoe et al. |
| 4,602,281 A | 7/1986 | Nagasaki et al. |
| 4,604,992 A | 8/1986 | Sato |
| 4,622,954 A | 11/1986 | Arakawa et al. |
| 4,625,236 A | 11/1986 | Fujimori et al. |
| 4,633,304 A | 12/1986 | Nagasaki |
| 4,643,170 A | 2/1987 | Miyazaki et al. |
| 4,646,721 A | 3/1987 | Arakawa |
| 4,651,201 A | 3/1987 | Schoolman |
| 4,656,508 A | 4/1987 | Yokota |
| 4,682,219 A | 7/1987 | Arakawa et al. |
| 4,684,222 A | 8/1987 | Borrelli et al. |
| 4,692,608 A | 9/1987 | Cooper et al. |
| 4,697,208 A | 9/1987 | Eino |
| 4,713,683 A | 12/1987 | Fujimori et al. |
| 4,714,319 A | 12/1987 | Zeevi et al. |
| 4,720,178 A | 1/1988 | Nishioka et al. |
| 4,741,327 A | 5/1988 | Yabe |
| 4,746,203 A | 5/1988 | Nishioka et al. |
| 4,757,805 A | 7/1988 | Yabe |
| 4,768,513 A | 9/1988 | Suzuki |
| 4,784,133 A | 11/1988 | Mackin |
| 4,803,550 A | 2/1989 | Yabe et al. |
| 4,803,562 A | 2/1989 | Eino |
| 4,809,680 A | 3/1989 | Yabe |
| 4,819,065 A | 4/1989 | Eino |
| 4,827,907 A | 5/1989 | Tashiro |
| 4,827,909 A | 5/1989 | Kato et al. |
| 4,831,456 A | 5/1989 | Takamura et al. |
| 4,832,003 A | 5/1989 | Yabe |
| 4,832,033 A | 5/1989 | Maher et al. |
| 4,857,724 A | 8/1989 | Snoeren |
| 4,862,873 A | 9/1989 | Yajima et al. |
| 4,866,526 A | 9/1989 | Ams et al. |
| 4,869,256 A | 9/1989 | Kanno et al. |
| 4,873,572 A | 10/1989 | Miyazaki et al. |
| 4,884,133 A | 11/1989 | Kanno et al. |
| 4,905,670 A | 3/1990 | Adair |
| 4,926,257 A | 5/1990 | Miyazaki |
| 4,934,339 A | 6/1990 | Kato |
| 4,939,573 A | 7/1990 | Teranishi et al. |
| 4,953,539 A | 9/1990 | Nakamura et al. |
| 4,967,269 A | 10/1990 | Sasagawa et al. |
| 4,986,642 A | 1/1991 | Yokota et al. |
| 4,998,972 A | 3/1991 | Chin et al. |
| 5,010,875 A | 4/1991 | Kato |
| 5,021,888 A | 6/1991 | Kondou et al. |
| 5,022,399 A | 6/1991 | Biegelisen |
| 5,029,574 A | 7/1991 | Shimamura et al. |
| 5,122,650 A | 6/1992 | McKinley |
| 5,166,787 A | 11/1992 | Irion |
| 5,184,223 A | 2/1993 | Mihara |
| 5,187,572 A | 2/1993 | Nakamura et al. |
| 5,191,203 A | 3/1993 | McKinley |
| 5,216,512 A | 6/1993 | Bruijns et al. |
| 5,219,292 A | 6/1993 | Dickirson et al. |
| 5,222,477 A | 6/1993 | Lia |
| 5,233,416 A | 8/1993 | Inoue |
| 5,264,925 A | 11/1993 | Shipp et al. |
| 5,301,090 A | 4/1994 | Hed |
| 5,306,541 A | 4/1994 | Kasatani |
| 5,311,600 A | 5/1994 | Aghajan et al. |
| 5,323,233 A | 6/1994 | Yamagami et al. |
| 5,325,847 A | 7/1994 | Matsuno |
| 5,335,662 A | 8/1994 | Kimura et al. |
| 5,343,254 A | 8/1994 | Wada et al. |
| 5,363,135 A | 11/1994 | Inglese |
| 5,376,960 A | 12/1994 | Wurster |
| 5,408,268 A | 4/1995 | Shipp |
| 5,430,475 A | 7/1995 | Goto et al. |
| 5,432,543 A | 7/1995 | Hasegawa et al. |
| 5,444,574 A | 8/1995 | Ono et al. |
| 5,450,243 A | 9/1995 | Nishioka |
| 5,471,237 A | 11/1995 | Shipp |
| 5,494,483 A | 2/1996 | Adair |
| 5,498,230 A | 3/1996 | Adair |
| 5,512,940 A | 4/1996 | Takasugi et al. |
| 5,547,455 A | 8/1996 | McKenna et al. |
| 5,557,324 A | 9/1996 | Wolff |
| 5,575,754 A | 11/1996 | Konomura |
| 5,588,948 A | 12/1996 | Takahashi et al. |
| 5,594,497 A | 1/1997 | Ahern et al. |
| 5,598,205 A | 1/1997 | Nishioka |
| 5,603,687 A | 2/1997 | Hori et al. |
| 5,604,531 A | 2/1997 | Iddan et al. |
| 5,607,436 A | 3/1997 | Pratt et al. |
| 5,668,596 A | 9/1997 | Vogel |
| 5,673,147 A | 9/1997 | McKinley |
| 5,700,236 A | 12/1997 | Sauer et al. |
| 5,712,493 A | 1/1998 | Mori et al. |
| 5,728,044 A | 3/1998 | Shan |
| 5,751,341 A | 5/1998 | Chaleki et al. |
| 5,754,280 A | 5/1998 | Kato et al. |
| 5,784,098 A | 7/1998 | Shoji et al. |
| 5,792,045 A | 8/1998 | Adair |
| 5,797,837 A | 8/1998 | Minami |
| 5,819,736 A | 10/1998 | Avny et al. |
| 5,827,176 A | 10/1998 | Tanaka et al. |
| 5,847,394 A | 12/1998 | Alfano et al. |
| 5,905,597 A | 5/1999 | Mizouchi et al. |
| 5,907,178 A | 5/1999 | Baker et al. |
| 5,909,633 A | 6/1999 | Haji et al. |
| 5,928,137 A | 7/1999 | Green |
| 5,929,901 A | 7/1999 | Adair et al. |
| 5,940,126 A | 8/1999 | Kimura |
| 5,944,655 A | 8/1999 | Becker |
| 5,984,860 A | 11/1999 | Shan |
| 5,986,693 A | 11/1999 | Adair et al. |
| 6,001,084 A | 12/1999 | Riek et al. |
| 6,006,119 A | 12/1999 | Soller et al. |
| 6,009,189 A | 12/1999 | Schaack |
| 6,010,449 A | 1/2000 | Selmon et al. |
| 6,039,693 A | 3/2000 | Seward et al. |
| 6,043,839 A | 3/2000 | Adair et al. |
| 6,075,235 A | 6/2000 | Chun |
| 6,099,475 A | 8/2000 | Seward et al. |
| 6,124,883 A | 9/2000 | Suzuki et al. |
| 6,129,672 A | 10/2000 | Seward et al. |
| 6,134,003 A | 10/2000 | Tearney et al. |
| 6,139,490 A | 10/2000 | Breidenthal et al. |
| 6,142,930 A | 11/2000 | Ito et al. |
| 6,148,227 A | 11/2000 | Wagnieres et al. |
| 6,156,626 A | 12/2000 | Bothra |
| 6,177,984 B1 | 1/2001 | Jacques |
| 6,178,346 B1 | 1/2001 | Amundson et al. |
| 6,184,923 B1 | 2/2001 | Miyazaki |
| 6,206,825 B1 | 3/2001 | Tsuyuki |
| 6,240,312 B1 | 5/2001 | Alfano et al. |
| 6,260,994 B1 | 7/2001 | Matsumoto et al. |
| 6,281,506 B1 | 8/2001 | Fujita et al. |
| 6,284,223 B1 | 9/2001 | Luiken |
| 6,327,374 B1 | 12/2001 | Piironen et al. |
| 6,331,156 B1 | 12/2001 | Haefele et al. |
| 6,409,658 B1 | 6/2002 | Mitsumori |
| 6,416,463 B1 | 7/2002 | Tsuzuki et al. |
| 6,417,885 B1 | 7/2002 | Suzuki et al. |
| 6,449,006 B1 | 9/2002 | Shipp |
| 6,459,919 B1 | 10/2002 | Lys et al. |
| 6,464,633 B1 | 10/2002 | Hosoda et al. |
| 6,476,851 B1 | 11/2002 | Nakamura |
| 6,485,414 B1 | 11/2002 | Neuberger |
| 6,533,722 B2 | 3/2003 | Nakashima |
| 6,547,721 B1 | 4/2003 | Higuma et al. |
| 6,659,940 B2 | 12/2003 | Adler |
| 6,670,636 B2 | 12/2003 | Hayashi et al. |
| 6,692,430 B2 | 2/2004 | Adler |
| 6,697,110 B1 | 2/2004 | Jaspers et al. |
| 6,900,527 B1 | 5/2005 | Miks et al. |
| 6,943,837 B1 | 9/2005 | Booth |
| 6,976,956 B2 | 12/2005 | Takahashi et al. |

(56) References Cited

U.S. PATENT DOCUMENTS

| | | | |
|---|---|---|---|
| 6,984,205 B2 | 1/2006 | Gazdzinski |
| 7,019,387 B1 | 3/2006 | Miks et al. |
| 7,030,904 B2 | 4/2006 | Adair et al. |
| 7,106,910 B2 | 9/2006 | Acharya et al. |
| 7,116,352 B2 | 10/2006 | Yaron |
| 7,123,301 B1 | 10/2006 | Nakamura et al. |
| 7,127,280 B2 | 10/2006 | Dauga |
| 7,133,073 B1 | 11/2006 | Neter |
| 7,154,527 B1 | 12/2006 | Goldstein et al. |
| 7,189,971 B2 | 3/2007 | Spartiotis et al. |
| 7,308,296 B2 | 12/2007 | Lys et al. |
| 7,347,817 B2 | 3/2008 | Glukhovsky et al. |
| 7,355,625 B1 | 4/2008 | Mochida et al. |
| 7,804,985 B2 | 9/2010 | Szawerenko et al. |
| 8,179,428 B2 | 5/2012 | Minami |
| 8,194,121 B2 | 6/2012 | Blumzvig et al. |
| 8,263,438 B2 | 9/2012 | Seah et al. |
| 8,438,730 B2 | 5/2013 | Ciminelli |
| 2001/0017649 A1 | 8/2001 | Yaron |
| 2001/0031912 A1 | 10/2001 | Adler |
| 2001/0040211 A1 | 11/2001 | Nagaoka |
| 2001/0051766 A1 | 12/2001 | Gazdzinski |
| 2002/0089586 A1 | 7/2002 | Suzuki et al. |
| 2002/0103417 A1 | 8/2002 | Gazdzinski |
| 2002/0154215 A1 | 10/2002 | Schechterman et al. |
| 2002/0198439 A1 | 12/2002 | Mizuno |
| 2003/0171648 A1 | 9/2003 | Yokoi et al. |
| 2003/0171649 A1 | 9/2003 | Yokoi et al. |
| 2003/0171652 A1 | 9/2003 | Yokoi et al. |
| 2003/0174208 A1 | 9/2003 | Glukhovsky et al. |
| 2003/0174409 A1 | 9/2003 | Nagaoka |
| 2004/0019255 A1 | 1/2004 | Sakiyama |
| 2004/0197959 A1 | 10/2004 | Ujiie et al. |
| 2005/0165279 A1 | 7/2005 | Adler et al. |
| 2005/0259487 A1 | 11/2005 | Glukhovsky et al. |
| 2005/0267328 A1 | 12/2005 | Blumzvig et al. |
| 2006/0158512 A1 | 7/2006 | Iddan et al. |
| 2008/0229573 A1 | 9/2008 | Wood et al. |
| 2009/0147076 A1 | 6/2009 | Ertas |
| 2009/0266598 A1 | 10/2009 | Katagiri et al. |
| 2009/0294978 A1 | 12/2009 | Ota et al. |
| 2010/0283818 A1 | 11/2010 | Bruce et al. |
| 2011/0210441 A1 | 9/2011 | Lee et al. |
| 2012/0161312 A1 | 6/2012 | Hossain et al. |
| 2012/0274705 A1 | 11/2012 | Petersen et al. |
| 2013/0129334 A9* | 5/2013 | Wang et al. ............ 396/14 |
| 2014/0249368 A1 | 9/2014 | HU et al. |

FOREIGN PATENT DOCUMENTS

| | | |
|---|---|---|
| JP | H09-173288 A | 7/1997 |
| WO | 98/48449 A2 | 10/1998 |
| WO | 2013073578 A1 | 5/2013 |

OTHER PUBLICATIONS

International Application # PCT/US14/42825 Search Report dated Oct. 6, 2014.
U.S. Appl. No. 13/940,282 Office Action dated Jul. 31, 2015.
U.S. Appl. No. 14/179,577 Office Action dated Oct. 13, 2015.

* cited by examiner

HYBRID INTERCONNECT

FIELD OF THE INVENTION

The present invention relates generally to connection devices, and specifically to devices where space used is a premium.

BACKGROUND OF THE INVENTION

Space requirements in the field of integrated circuit utilization are a critical feature of the design of a system using integrated circuits. The smaller that an integrated circuit, and ancillary components such as conducting traces to the integrated circuit, can be made, the more integrated circuits can be produced for a given size of a silicon wafer. Other advantages for reduced size integrated circuits include the reduction in power requirements for operating the circuits.

SUMMARY OF THE INVENTION

An embodiment of the present invention provides a connector for connection to terminals of an integrated circuit, the connector including:
a dielectric substrate having a first side and a second side;
wire bond terminals, attached to the first side of the substrate and configured to receive wire bonds connected to a first set of the terminals of the integrated circuit; and
solder bump terminals, attached to the second side of the substrate so as to be insulated from the wire bond terminals, the solder bump terminals being configured to be coupled via solder balls with a second set of the terminals of the integrated circuit.

Typically, the solder bump terminals are arranged in a solder bump terminal configuration, and the second set of terminals of the integrated circuit are arranged in an integrated circuit terminal configuration which is congruent to the solder bump terminal configuration. In an embodiment, solder bump terminal configuration is rectilinear. Alternatively, the solder bump terminal configuration is non-rectilinear.

In a disclosed embodiment the solder bump terminals are equally spaced. Alternatively, the solder bump terminals are unevenly spaced.

In a further disclosed embodiment the wire bond terminals and the solder bump terminals are equal in number. Typically, the wire bond terminals and the solder bump terminals are aligned.

In a yet further disclosed embodiment the wire bond terminals and the solder bump terminals are misaligned.

There is further provided, according to an embodiment of the present invention embodiment, a method for connecting to terminals of an integrated circuit, the method including:
providing a dielectric substrate having a first side and a second side;
attaching wire bond terminals to the first side of the substrate, the wire bond terminals being configured to receive wire bonds connected to a first set of the terminals of the integrated circuit; and
attaching solder bump terminals to the second side of the substrate so as to be insulated from the wire bond terminals, the solder bump terminals being configured to be coupled via solder balls with a second set of the terminals of the integrated circuit.

There is further provided, according to an embodiment of the present invention, an endoscope, including:
an integrated circuit;
an imaging device formed on the integrated circuit; and
a connector for connection to terminals of the integrated circuit, the connector including:
a dielectric substrate having a first side and a second side;
wire bond terminals, attached to the first side of the substrate and configured to receive wire bonds connected to a first set of the terminals of the integrated circuit; and
solder bump terminals, attached to the second side of the substrate so as to be insulated from the wire bond terminals, the solder bump terminals being configured to be coupled via solder balls with a second set of the terminals of the integrated circuit.

There is further provided, according to an embodiment of the present invention, a method for forming an endoscope, including:
providing an integrated circuit having terminals;
implementing an imaging device on the integrated circuit;
attaching wire bond terminals to a first side of a dielectric substrate, the wire bond terminals being configured to receive wire bonds connected to a first set of the terminals of the integrated circuit; and
attaching solder bump terminals to a second side of the dielectric substrate so as to be insulated from the wire bond terminals, the solder bump terminals being configured to be coupled via solder balls with a second set of the terminals of the integrated circuit.

The present invention will be more fully understood from the following detailed description of the embodiments thereof, taken together with the drawings in which:

DETAILED DESCRIPTION OF EMBODIMENTS

Overview

In certain fields, such as invasive medical procedures, miniaturization of the equipment used is extremely beneficial. There is thus constant pressure to reduce the size of the elements of integrated circuits, including connections to the circuits.

A connection to an integrated circuit that reduces the space requirements of the connection would therefore be advantageous.

An embodiment of the present invention provides an integrated circuit connector that uses space on the connector in an efficient manner. The connector, herein also termed a hybrid connector, is formed on a dielectric substrate, which is typically planar and flexible. Wire bond terminals are attached to one side of the substrate, the wire bond terminals being configured to connect, via wire bonds, to a first set of terminals of an integrated circuit. Solder bump terminals are attached to a second side of the substrate, so as to be insulated from the wire bond terminals. The solder bump terminals are coupled, via respective solder balls, to a second set of terminals of the integrated circuit. Typically, in order for the solder bump terminals to couple to the second set of integrated circuit terminals, the two sets of terminals are arranged in congruent configurations.

Typically, although not necessarily, there are an equal number of wire bond terminals and solder bump terminals, and the two types of terminals may be aligned so that each wire bond terminal is "opposite" a respective solder bump terminal. Such a configuration leads to an efficient use of space on the hybrid connector. For example, if the separation between adjacent wire bond terminals, and between adjacent solder bump terminals, is 60 μm, then the connector has two terminals in a pitch of 60 μm.

The reduction in space requirements provided by embodiments of the present invention is advantageous in a number of fields, for example in the field of invasive or minimally invasive medical procedures where electronic equipment may need to be inserted into a patient. As a specific example, in a minimally invasive procedure an endoscope may need to be inserted into the patient, so that incorporating a hybrid connector, as is described herein, enables improved miniaturization of the endoscope, with consequent benefit to the patient.

DETAILED DESCRIPTION

Figure 1A:
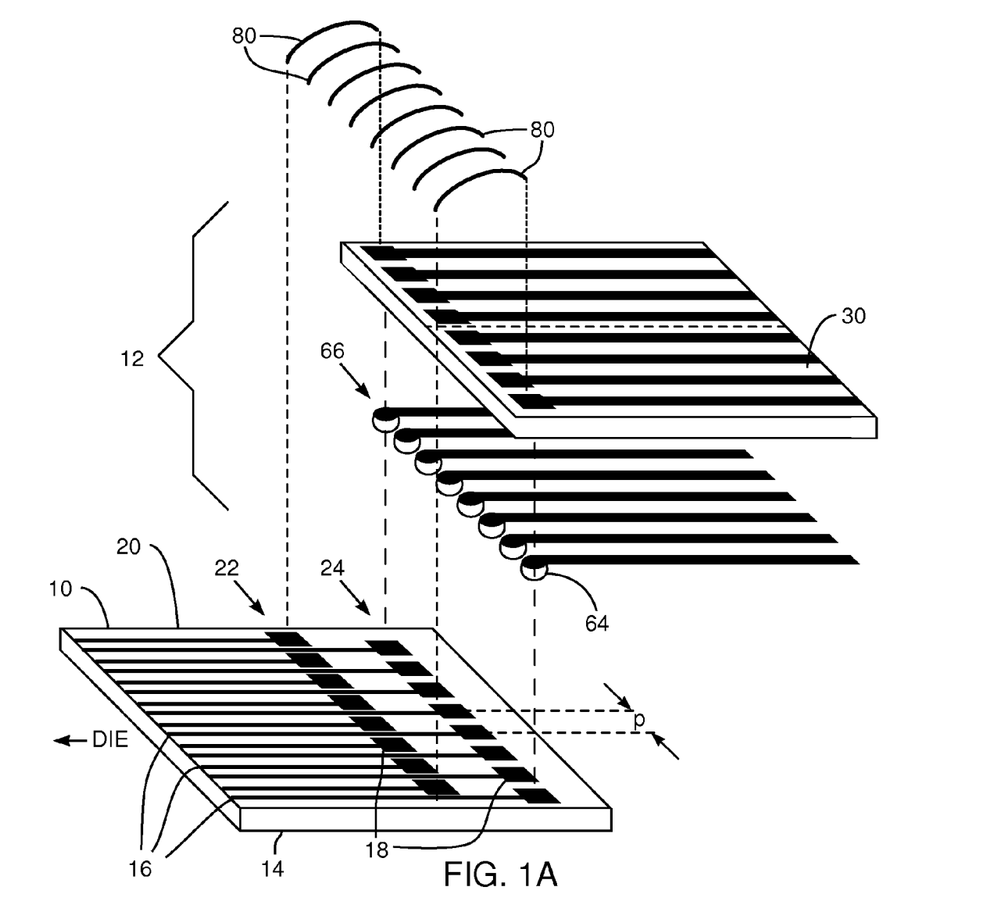
FIG. 1A is a schematic exploded view of an integrated circuit attached to a hybrid connector.
Figure 1B:
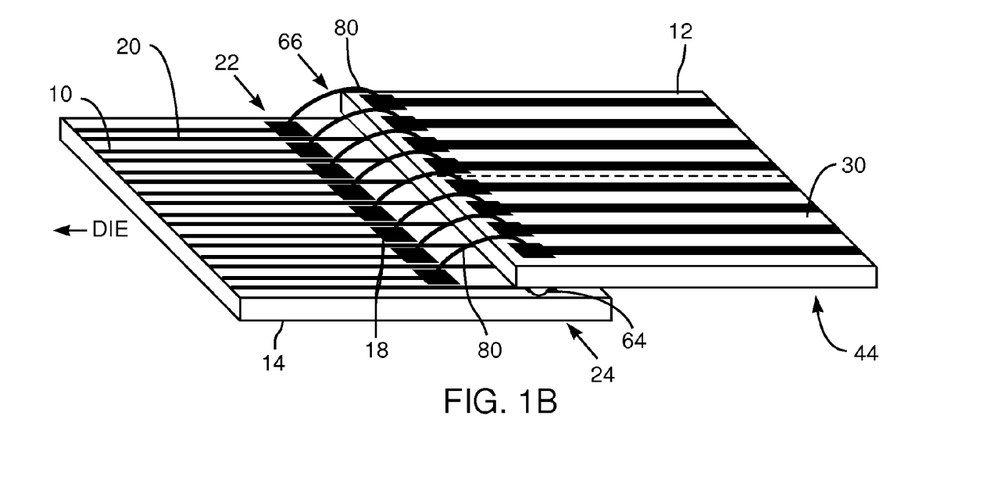
FIG. 1B is a schematic assembled view of the integrated circuit attached to the connector, according to embodiments of the present invention.

FIG. 1A is a schematic exploded view of an integrated circuit (IC) 10 attached to a hybrid connector 12, and FIG. 1B is a schematic assembled view of the IC attached to the connector, according to embodiments of the present invention. IC 10 is typically constructed as a die on an insulating substrate 14, and there are a number of conducting traces 16 leading from the die to generally similar IC conducting terminals 18 at the edge of the substrate. The IC conducting terminals at the edge of the substrate are used, as is explained further below, to connect elements of the die to components external to substrate 14. The connection is via hybrid connector 12. For simplicity in FIGS. 1A and 1B the die to which traces 16 connect is not shown, and the diagram illustrates the edge of IC 10.

In an embodiment of the present invention, IC conducting terminals 18 are assumed to be formed on an upper surface 20 of the substrate as a first row 22 and as a second row 24. Typically, rows 22 and 24 are rectilinear, i.e., are in a straight line, for simplicity of manufacture of IC 10, and this configuration is assumed in the following description, except where otherwise stated. However, there is no requirement that rows 22 and 24 be rectilinear, and in some embodiments of the present invention at least one of the rows is non-rectilinear. Thus, by way of example, in FIGS. 1A and 1B there are assumed to be eight conducting terminals in each row, the rows are assumed to be rectilinear, and there is a separation p between adjacent terminals within a row. However, it will be understood that embodiments of the present invention may be implemented for any convenient number of terminals in each row.

For simplicity, the following description relates to a section 30 of hybrid connector 12 which corresponds with IC 10 having four conducting terminals 18 in each of rows 22 and 24, but those having ordinary skill in the art will be able to adapt the following description for IC 10 with eight conducting terminals in each row, or for an IC with any convenient number of terminals in each row. While some elements of hybrid connector 12 are identified numerically in FIGS. 1A and 1B, for clarity the explanation of these elements is left to the description provided for FIGS. 2A, 2B, and 2C below.

Figure 2A:
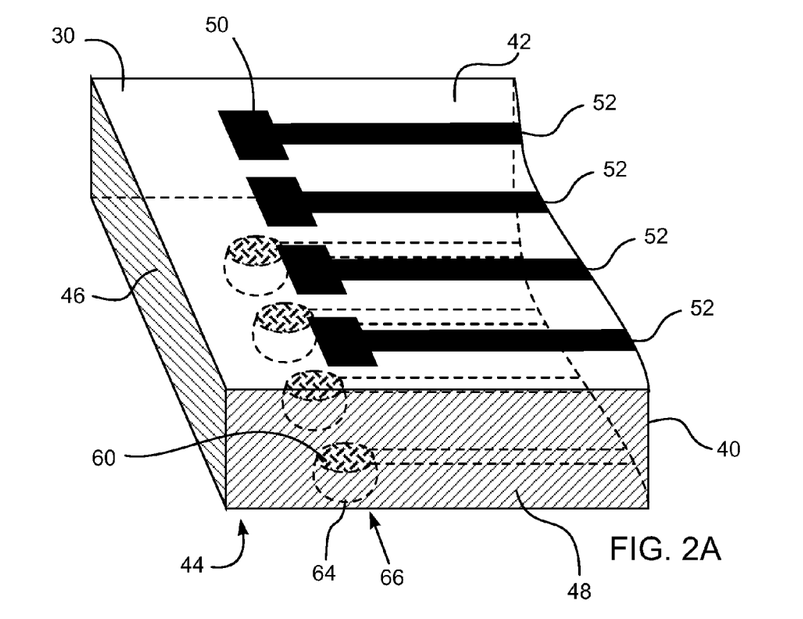
FIGS. 2A, 2B, and 2C are respective perspective, side, and front schematic diagrams of the hybrid connector, according to embodiments of the present invention.
Figure 2B:
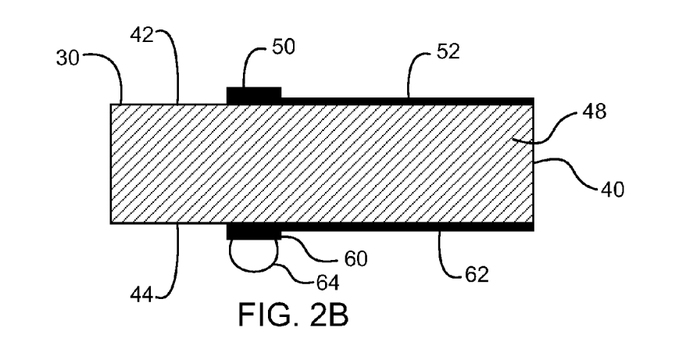
Figure 2C:
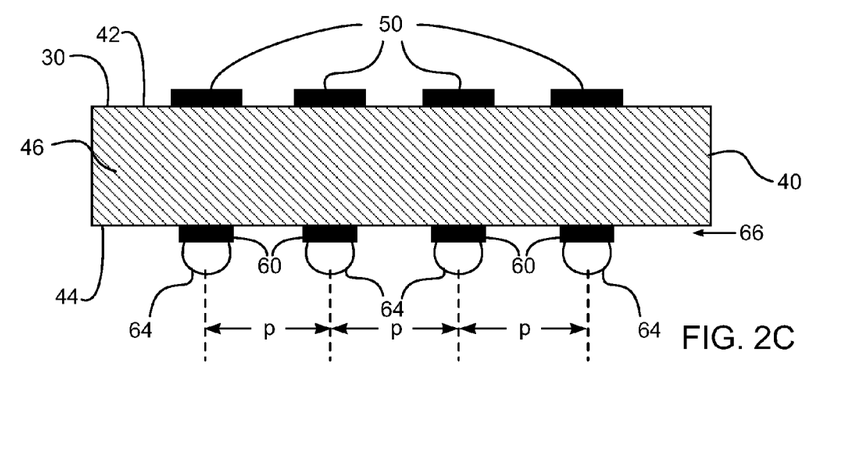

FIGS. 2A, 2B, and 2C are schematic views of section 30 of hybrid connector 12, according to embodiments of the present invention. FIG. 2A is a schematic perspective view, FIG. 2B is a schematic side view, and FIG. 2C is a schematic front view of section 30. Hybrid connector is assumed to be formed with an insulating, dielectric, substrate 40 which is in the form of a parallelepiped having an upper surface 42, a lower surface 44, a front surface 46, and a side surface 48. In the following description, the designations upper, lower, front, and side are for clarity for use with the figures, and it will be understood that connector 12 may be used in substantially any orientation. Typically, although not necessarily, substrate 40 is a flexible substrate.

Substantially similar wire bond conducting terminals 50 are formed on upper surface 42 and the terminals are connected to respective conducting traces 52; four terminals 50 connected to four traces 52 are illustrated for section 30. By way of example, terminals 50 are assumed to be rectangular.

Substantially similar solder bump conducting terminals 60 are formed on lower surface 44, and the solder bump terminals are connected to respective conducting traces 62; four terminals 60 connected to four traces 62 are illustrated for section 30. By way of example, terminals 60 are assumed to be circular. To each solder bump conducting terminal 60 a respective solder ball 64 is attached. Solder balls are also known as solder bumps or solder dots.

Solder bump terminals 60 are arranged on surface 44 so as to correspond in number and geometrical configuration with conducting terminals 18 in row 24. Thus, in section 30 four solder bump terminals 60 are arranged along a straight line row 66 with spacing p between the terminals.

Traces 52 and 62 are typically connected, at the opposite ends of the traces to wire bond terminals 50 and solder bump terminals 60, to equipment that uses IC 10. The connection may be directly to the equipment, or alternatively via cabling connected between the opposite ends of the traces and the equipment. For simplicity, the cabling and the equipment is not shown in FIGS. 1A, 1B, 2A, 2B, and 2C.

Returning to FIGS. 1A and 1B, to attach connector 12 to IC 10, substrate 40 is positioned so that solder balls 64 align with and contact conducting terminals 18 of row 24 of the integrated circuit. The solder balls may then be re-melted to produce an electrical connection, typically using an ultrasonic or alternatively a reflow solder process. Space remaining between the lower surface 44 of the connector, and upper surface 20 of the IC may then typically be filled with an electrically-insulating adhesive, which provides a better mechanical connection between IC 10 and connector 12 than just the re-melted solder balls.

To complete the connection between IC 10 and connector 12, terminals 50 of the hybrid connector are then connected to respective IC terminals 18 in row 22, using wire bonds 80.

Typically, wire bond terminals 50 correspond in number to the number of solder bump terminals 60. In addition, the wire bond terminals are usually aligned with the solder bump terminals, since the correspondence in number and alignment leads to an efficient use of the space available in connector 12. Such an efficient use of space is illustrated in FIGS. 2A, 2B, and 2C. In one embodiment, the wire bond terminals and the solder bump terminals are aligned, and p=60 µm. Such an arrangement provides two traces 52, 62 per 60 µm, measured in a direction orthogonal to the traces.

However, while the number of wire bond terminals 50 on connector 12 corresponds to the number of wire bond terminals 18 in row 22 of IC 10, there is no requirement that there is a correspondence between the number of wire bond terminals 50 and solder bump terminals 60. In connector 12 there is also no requirement that wire bond terminals 50 and solder bump terminals 60 are aligned. Thus, in some embodiments of the present invention the number of wire bond terminals 50 does not equal the number of solder bump terminals 60, and/or the two sets of terminals are misaligned.

The embodiments described above have assumed that solder bump terminals 60 of connector 12 are arranged in a rectilinear manner, i.e., in a straight line, and that adjacent terminals are equally spaced along the line. The same arrangement, i.e., equally spaced in a straight line, is assumed for terminals 18 in row 24 of IC 10. However, such a straight line, equally spaced arrangement is not a requirement for embodiments of the present invention, and examples of other possible arrangements of solder bump terminals 60 and terminals 18 of row 24 are described below.

Figure 3:
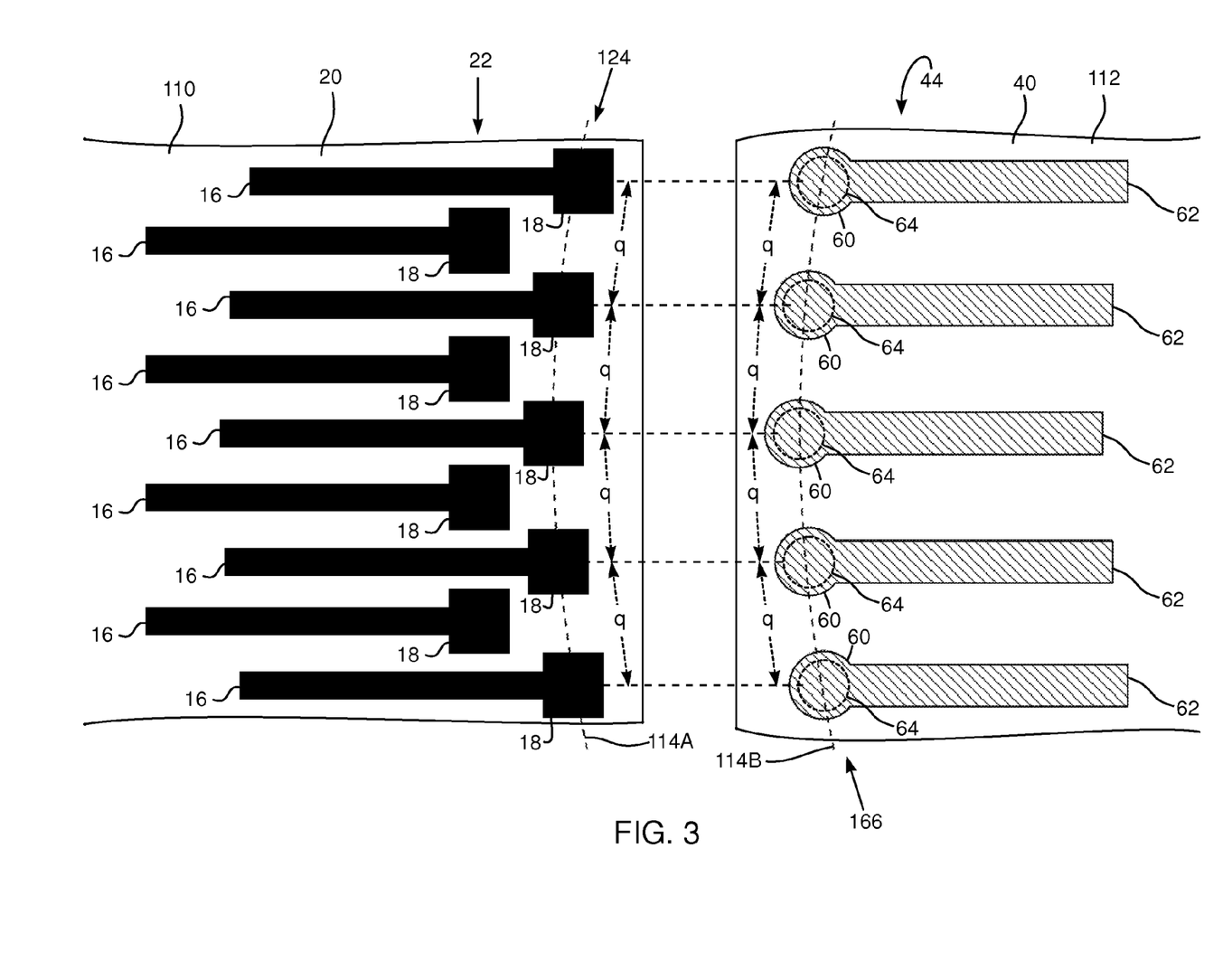
FIG. 3 is a schematic diagram illustrating a section of an integrated circuit and a section of a connector that connects to the integrated circuit, according to an alternative embodiment of the present invention.

FIG. 3 is a schematic diagram illustrating a section of an IC 110, and a section of a connector 112 that connects to IC 110, according to an embodiment of the present invention. Apart from the differences described below, the operations of IC 110 and connector 112 are generally similar to those of IC 10 and connector 12 (FIGS. 1A, 1B, 2A, 2B, and 2C), and elements indicated by the same reference numerals in ICs 110 and 10, and in connectors 112 and 12 are generally similar in construction and in operation. For simplicity, FIG. 3 only shows a portion of upper surface 20 of IC 110, and a corresponding portion of lower surface 44 of substrate 40 of connector 112. The figure is drawn from the point of view of a person looking at the IC 110 and connector 112 from above, so that elements on upper surface 20 are above the plane of the paper, whereas elements on lower surface 44 are "beneath" connector 112, i.e., are below the plane of the paper. For clarity, in the illustration of connector 112, only elements on lower surface 44 of the connector are shown.

In IC 110 upper surface 20 has first row of terminals 22, comprising conducting terminals 18 connected to respective traces 16. IC 110 comprises a second row 124 of terminals 18, wherein, in contrast to row 24 of IC 10, the terminals are arranged along a curved line 114A. Typically, although not necessarily, terminals 18 that are arranged along line 114A are equally spaced, and in the following description a spacing "q" between adjacent terminals of row 124 is assumed.

Connector 112 comprises a row 166 of solder bump terminals 60 connected to traces 62, and solder balls 64 are mounted on terminals 60. In contrast to row 66 of connector 12, solder bump terminals 60 in row 166 are arranged along a curved line 114B which is congruent to curved line 114A. In addition, the arrangement of the solder bump terminals 60 along line 114B is congruent to the arrangement of terminals 18 along line 114A, so that terminals 60 in row 166 have spacing q between adjacent terminals 60.

As for connector 12 and IC 10, in attaching connector 112 to IC 110 substrate 40 is positioned so that solder balls 64 in row 166 align with and contact conducting terminals 18 of row 124 of IC 110. The solder balls are then re-melted to form an electrical connection between terminals 18 and terminals 60.

Figure 4:
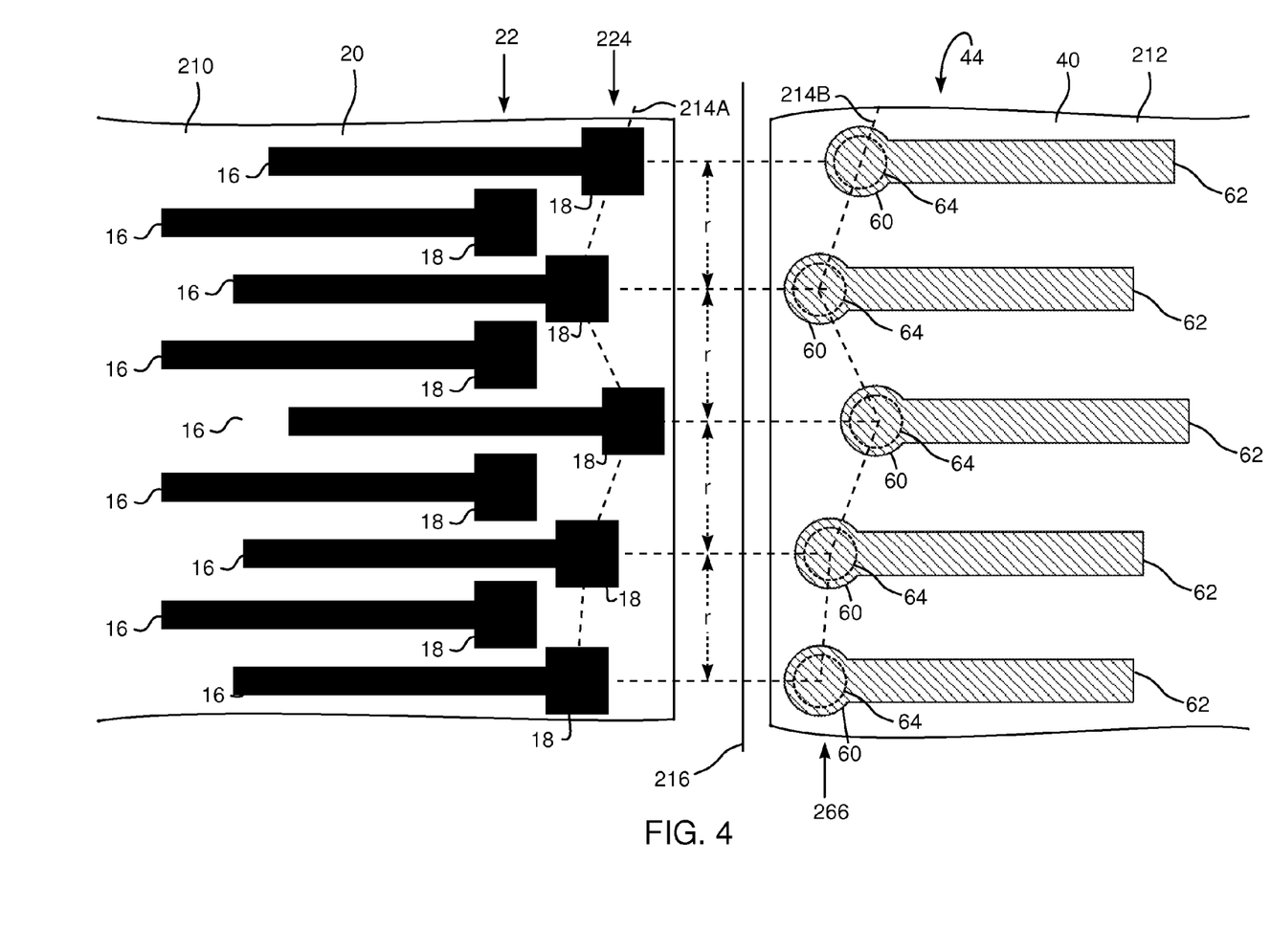
FIG. 4 is a schematic diagram illustrating a section of an integrated circuit and a section of a connector that connects to the integrated circuit, according to a further alternative embodiment of the present invention.

FIG. 4 is a schematic diagram illustrating a section of an IC 210, and a section of a connector 212 that connects to IC 210, according to an embodiment of the present invention. Apart from the differences described below, the operations of IC 210 and connector 212 are generally similar to those of IC 10 and connector 12 (FIGS. 1A, 1B, 2A, 2B, 2C, and 3), and elements indicated by the same reference numerals in ICs 210 and 10, and in connectors 212 and 12 are generally similar in construction and in operation.

The illustration of IC 210 and connector 212 is generally as for IC 110 and connector 112 (FIG. 3), so that IC 210 and connector 212 are drawn from the point of view of a person looking at IC 210 and connector 212 from above. As for FIG. 3, in FIG. 4 in the illustration of connector 212, only elements on lower surface 44 of the connector are shown.

In IC 210 upper surface 20 has first row of terminals 22, comprising conducting terminals 18 connected to respective traces 16. IC 210 comprises a second row 224 of terminals 18, which, in contrast to row 24 of IC 10 (and row 124 of IC 110), has terminals that are arranged along an irregular "zig-zag" line 214A. Typically, although not necessarily, terminals 18 are arranged to be equally spaced if measured along a line 216, orthogonal to traces 16, and in the following description a spacing "r" along line 216 is assumed.

Connector 212 comprises a row 266 of solder bump terminals 60 connected to traces 62, and solder balls 64 are mounted on terminals 60. In contrast to row 66 of connector 12, solder bump terminals 60 in row 266 are arranged along an irregular line 214B which is congruent to irregular line 214A. In addition, the arrangement of solder bump terminals 60 along line 214B is congruent to the arrangement of terminals 18 along line 214A, so that terminals 60 in row 266 have spacing r measured with respect to line 216.

To attach connector 212 to IC 210 substrate 40 is positioned so that solder balls 64 in row 266 align with and contact conducting terminals 18 of row 224 of IC 110. The solder balls are then re-melted to form an electrical connection between terminals 18 and terminals 60.

Figure 5:
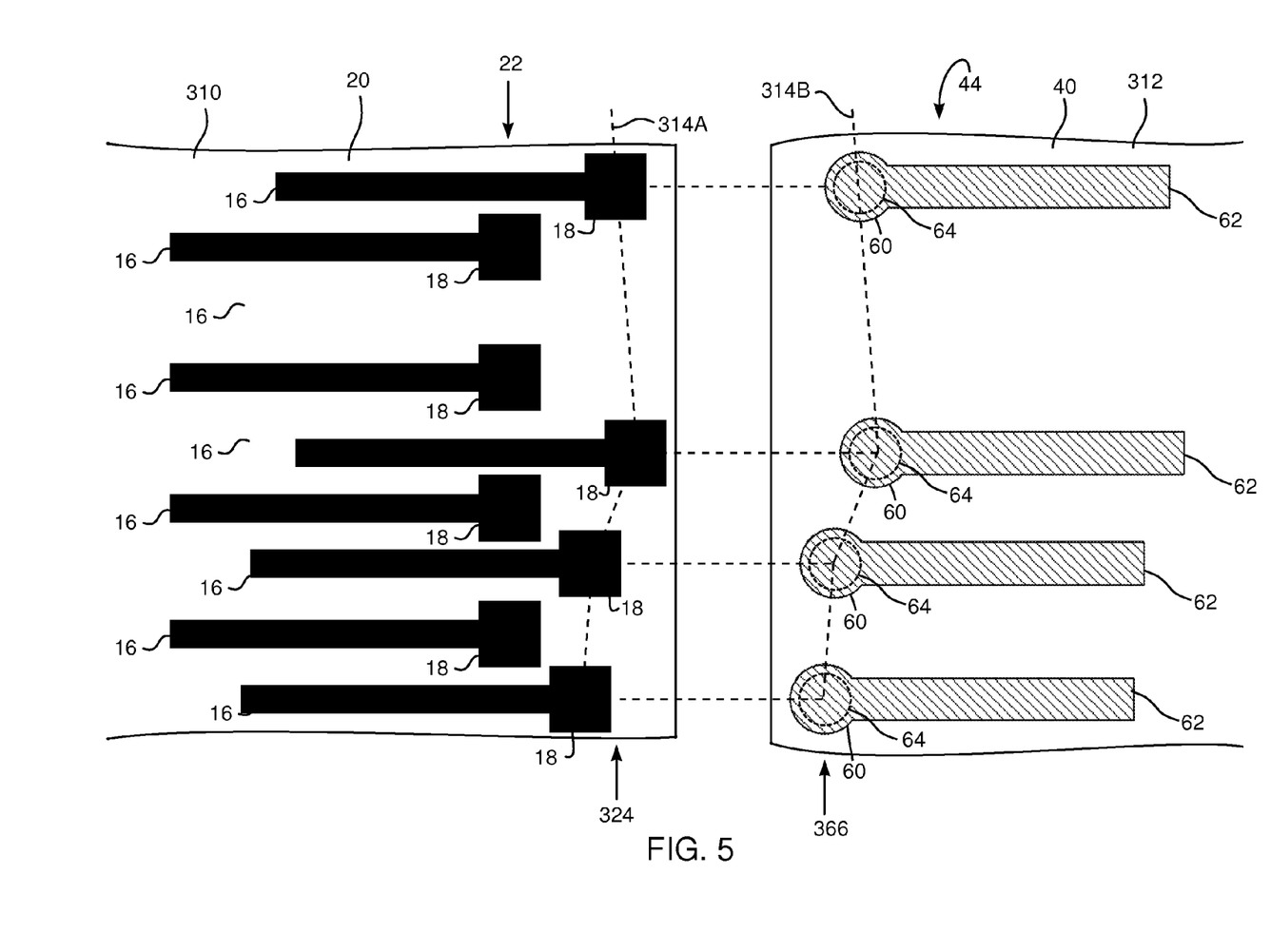
FIG. 5 is a schematic diagram illustrating a section of an integrated circuit and a section of a connector that connects to the integrated circuit, according to a yet further alternative embodiment of the present invention.

FIG. 5 is a schematic diagram illustrating a section of an IC 310, and a section of a connector 312 that connects to IC 310, according to an embodiment of the present invention. Apart from the differences described below, the operations of IC 310 and connector 312 are generally similar to those of IC 10 and connector 12 (FIGS. 1A, 1B, 2A, 2B, and 2C), and elements indicated by the same reference numerals in ICs 310 and 10, and in connectors 312 and 12 are generally similar in construction and in operation.

The illustration of IC 310 and connector 312 is generally as for IC 110 and connector 112 (FIG. 3), so that IC 310 and connector 312 are drawn from the point of view of a person looking at IC 310 and connector 312 from above. In FIG. 5 in the illustration of connector 312, only elements on lower surface 44 of the connector are shown.

In IC 310 upper surface 20 has first row of terminals 22, comprising conducting terminals 18 connected to respective traces 16. IC 310 comprises a second row 324 of terminals 18, which are arranged along an irregular non-linear line 314A. In addition to being arranged on non-linear line 314A, terminals 18 are arranged to be unevenly spaced between adjacent terminals 18.

Connector 312 comprises a row 366 of solder bump terminals 60 connected to traces 62, and solder balls 64 are mounted on terminals 60. Solder bump terminals 60 in row 366 are arranged along an irregular non-linear line 314B which is congruent to irregular non-linear line 314A. In addition, the arrangement of solder bump terminals 60 along line 314B is congruent to the arrangement of terminals 18 along line 314A. Consequently, the different spacings between adjacent bump terminals 60 are congruent to the different spacings between adjacent terminals 18.

The attachment of connector 312 to IC 310 is substantially as described above for attaching connector 212 to IC 210.

Figure 6:
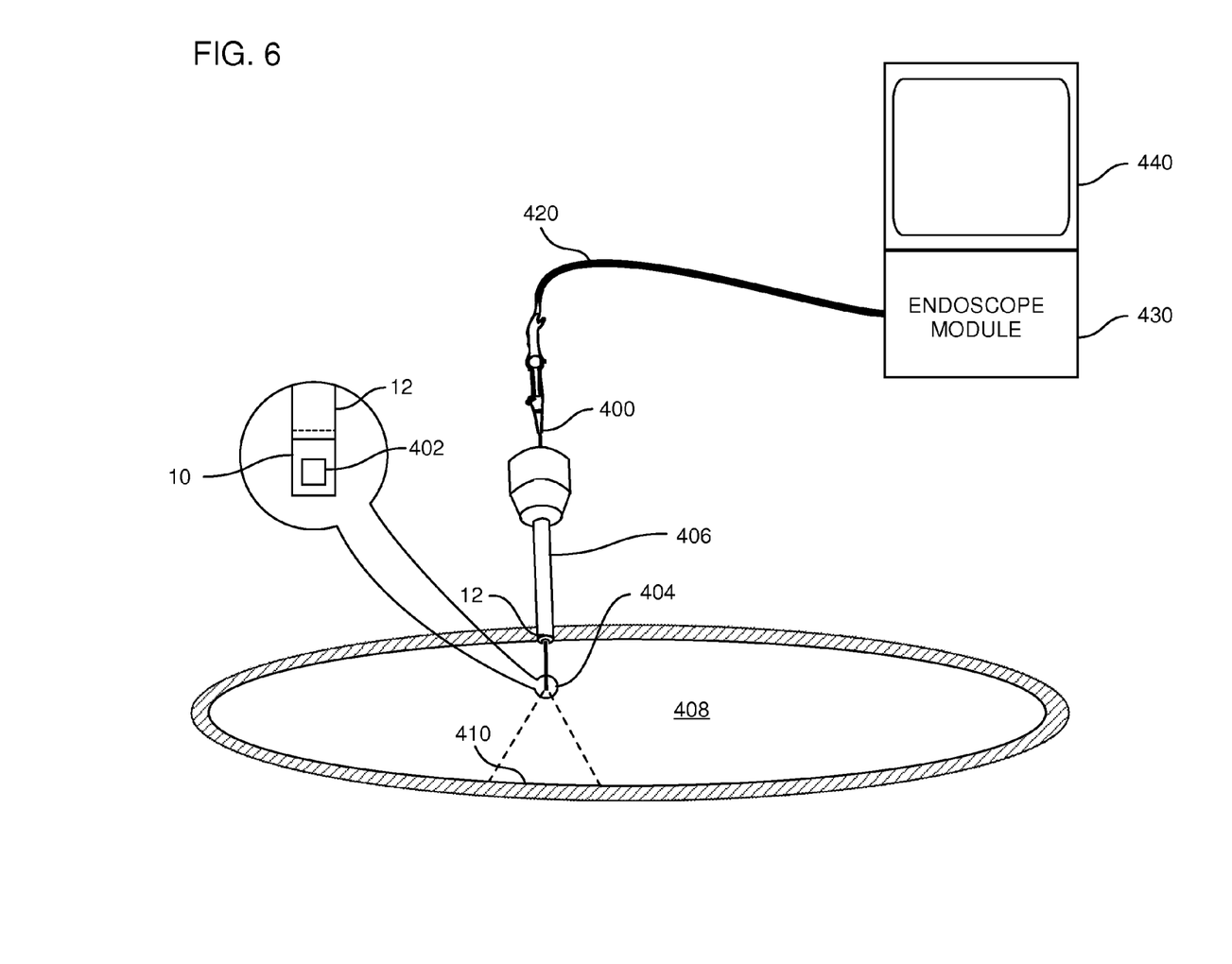
FIG. 6 is a schematic diagram illustrating an endoscope using a hybrid connector, according to an embodiment of the present invention.

FIG. 6 is a schematic diagram illustrating an endoscope 400 using a hybrid connector, according to an embodiment of the present invention. For clarity and by way of example, in the following description endoscope 400 is assumed to use hybrid connector 12 connected to IC 10 (described above), and those having ordinary skill in the art will be able to adapt the description for other embodiments of the present invention, such as hybrid connectors 112, 212, and 312, and integrated circuits other than IC 10.

An imaging device 402 is formed on IC 10, the imaging device typically comprising a CCD (charge coupled device) which acquires an image of an object viewed using the endoscope. (Imaging device 402 typically includes corresponding optics, but for simplicity the optics are not illustrated in FIG. 6.) Imaging device 402 is located at a distal end 404 of the endoscope, and the distal end is inserted, via a trocar 406 into a body cavity 408 of a patient, so that device 402 acquires an image of walls 410 of the patient's body cavity. Also located at distal end 404 is hybrid connector 12, which connects to IC 10, as described above, and the traces of the hybrid connector connect (at the opposite ends of the traces from terminals 50 and 60) to endoscope cabling 420.

The miniaturization provided by hybrid connector 12 allows the diameter of distal end 404 to be reduced compared to distal ends of prior art endoscopes, and the reduced diameter is beneficial to the patient whose body cavity is being imaged.

An endoscope module 430 is connected to cabling 420, the module serving to provide power and driving signals to IC 10 and imaging device 402 via the cabling and hybrid connector 12. The module also receives image signals from device 402 via the cabling and the hybrid connector, and the module processes the signals so as to display an image of walls 410 on a screen 440. Endoscope modules such as module 430 are well known in the art, and for simplicity will not further be described here.

While the above description refers to use of a hybrid connector in an endoscope, it will be understood that the reduced size provided by embodiments of the present invention may be advantageously implemented in other fields, such as, but not being limited to, non-medical fields where size reduction of components is important. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Apparatus, comprising:
   an integrated circuit comprising a first set of terminals and a second set of terminals:
   wire bonds connected to the first set of terminals; and
   a connector connected to the integrated circuit, the connector comprising:
   a dielectric substrate having a first side and a second side;
   wire bond terminals, attached to the first side of the substrate, that receive the wire bonds; and
   solder bump terminals, attached to the second side of the substrate so as to be insulated from the wire bond terminals, and coupled via solder balls with the second set of terminals of the integrated circuit, wherein the solder bump terminals are arranged in a solder bump terminal configuration, and the second set of terminals of the integrated circuit are arranged in an integrated circuit terminal configuration which is congruent to the solder bump terminal configuration.

2. The apparatus according to claim 1, wherein the solder bump terminal configuration is rectilinear.

3. The apparatus according to claim 1, wherein the solder bump terminal configuration is non-rectilinear.

4. The apparatus according to claim 1, wherein the solder bump terminals are equally spaced.

5. The apparatus according to claim 1, wherein the solder bump terminals are unevenly spaced.

6. The apparatus according to claim 1, wherein the wire bond terminals and the solder bump terminals are equal in number.

7. The apparatus according to claim 6, wherein the wire bond terminals and the solder bump terminals are aligned, such that each wire bond terminal is opposite a respective solder bump terminal.

8. The apparatus according to claim 6, wherein the wire bond terminals and the solder bump terminals are misaligned.

9. An endoscope, comprising:
   an integrated circuit comprising a first set of terminals and a second set of terminals;
   wire bonds connected to the first set of terminals;
   an imaging device formed on the integrated circuit; and
   a connector connected the integrated circuit, the connector comprising:
   a dielectric substrate having a first side and a second side;
   wire bond terminals, attached to the first side of the substrate, that receive the wire bonds; and
   solder bump terminals, attached to the second side of the substrate so as to be insulated from the wire bond terminals coupled via solder balls with the second set of terminals of the integrated circuit, wherein the solder bump terminals are arranged in a solder bump terminal configuration, and the second set of terminals of the integrated circuit are arranged in an integrated circuit terminal configuration which is congruent to the solder bump terminal configuration.

* * * * *